United States Patent [19]

Nandagiri et al.

[11] Patent Number: 5,000,948
[45] Date of Patent: Mar. 19, 1991

[54] FILM RELEASE OF HAIR-TREATING COMPOSITIONS

[75] Inventors: Arun Nandagiri, Libertyville, Ill.; Joseph C. Hourihan, Little Falls, N.J.; Kathy Pilko, Mahwah, N.J.; Alice B. Benson, Paterson, N.J.

[73] Assignee: Playtex Beauty Care, Inc., Stamford, Conn.

[21] Appl. No.: 369,439

[22] Filed: Jun. 20, 1989

[51] Int. Cl.$^5$ .................. A61K 7/09; A45D 7/04; A45D 2/00
[52] U.S. Cl. .................. 424/71; 132/203; 132/221; 132/222; 424/411; 424/401
[58] Field of Search .................. 424/486, 71, 72, 78, 424/411, 401; 132/202, 203, 207, 208, 210, 221, 222

[56] References Cited

U.S. PATENT DOCUMENTS

| | | | |
|---|---|---|---|
| 2,869,559 | 1/1959 | Moore | 132/203 |
| 3,465,759 | 9/1969 | Haefele | 132/7 |
| 3,822,238 | 7/1974 | Blair et al. | 260/75 |
| 3,837,349 | 9/1974 | Jedzinak et al. | 132/7 |
| 3,955,586 | 5/1976 | Hartsough | 132/7 |
| 3,966,902 | 6/1976 | Chromecek | 424/78 X |
| 3,975,350 | 8/1976 | Hudgin et al. | 260/30.4 |
| 4,044,782 | 8/1977 | Adrion | 132/7 |
| 4,156,066 | 5/1979 | Gould et al. | 528/73 |
| 4,156,067 | 5/1979 | Gould | 528/73 |
| 4,255,550 | 3/1981 | Gould | 528/44 |
| 4,359,558 | 11/1982 | Gould et al. | 525/454 |
| 4,408,023 | 10/1983 | Gould et al. | 525/454 |
| 4,424,305 | 1/1984 | Gould et al. | 525/127 |
| 4,439,583 | 3/1984 | Gould et al. | 525/127 |
| 4,439,584 | 3/1984 | Gould et al. | 525/127 |
| 4,439,585 | 3/1984 | Gould et al. | 525/127 |
| 4,451,635 | 5/1984 | Gould et al. | 528/71 |
| 4,454,309 | 6/1984 | Gould et al. | 525/454 |
| 4,490,423 | 12/1984 | Gould et al. | 428/36 |
| 4,496,535 | 1/1985 | Gould et al. | 424/19 |
| 4,729,914 | 3/1988 | Kliment et al. | 428/36 |
| 4,743,673 | 5/1988 | Johnston et al. | 528/60 |
| 4,789,720 | 12/1988 | Teffenhart | 528/76 |
| 4,848,377 | 7/1989 | Bires et al. | 132/222 |

FOREIGN PATENT DOCUMENTS 55-45414  3/1980  Japan.

*Primary Examiner*—Merrell C. Cashion, Jr.
*Assistant Examiner*—Susan S. Rucker
*Attorney, Agent, or Firm*—Stewart J. Fried

[57] ABSTRACT

A hair-waving product comprises a polyurethane film containing a hair-waving composition which is released from the polyurethane film when the film is contacted with wet hair. The invention also relates to a process of hair waving comprising rolling the polyurethane film into wet hair and allowing sufficient hair-waving treatment time to release the hair-waving composition.

10 Claims, No Drawings

FILM RELEASE OF HAIR-TREATING COMPOSITIONS

BACKGROUND OF THE INVENTION

1. Field of the Invention

The present invention relates to a hair-treatment product and a method for its use. More specifically, the present invention relates to a hair-waving product comprising a hydrophilic polymeric film containing a releasable hair-waving composition, and a method for its use.

2. Description of the Related Art

The permanent waving of hair is a process whereby a wave or curl is formed in an individual's hair. In all forms of permanent waving, chemicals are used to impart the wave in the hair. These processes have several general advantages, namely, that women can readily effect a change in their hair style, which is long-lasting, and waves can be imparted only to those sections of the hair where it is desired.

In the general waving process, which includes permanent waves and body waves, an individual's hair is first shampooed and the wet hair is then separated into swatches or sections and rolled or wrapped around a mandrel (usually a curler) using paper end wraps and secured in the general shape of the desired wave or curl.

Thereafter a keratin-reducing composition is separately applied to the wound hair swatch and a sufficient period of time is allowed for the keratin-reducing composition to break the disulfide linkages present in the keratin of the hair and to cause the hair to assume its new, desired shape. The wound hair swatch is then rinsed with water and blotted. In addition, the wound hair swatch may be neutralized, which process reforms the chemical bonds in the new wound configuration, thereby giving permanence to the style. The hair is then removed from the mandrel, rinsed and set.

The permanent waving process which is traditionally employed, however, suffers from several disadvantages. It is a cumbersome process, requiring the wrapping of the hair in addition to the separate application of the hair waving composition. Also, the application of the hair-waving composition is often inexact, producing dripping of the composition on the skin with possible irritation.

Furthermore, due care must be exercised to avoid possible contact with the eyes. An additional detriment is the unpleasant odor which emanates from the solution employed in the traditional permanent waving process.

SUMMARY OF THE INVENTION

It is, accordingly, an object of the present invention to provide a hair-treatment product which greatly facilitates its application to the hair, reduces the dripping and spillage usually associated with hair-treatment compositions, and produces less odor during the hair-treatment process.

The foregoing and other objects are achieved by providing a hair-treatment product comprising a hydrophilic, polymeric film containing a hair-treatment composition therein.

Among the hydrophilic, polymeric films that can be employed, but not limited thereto, are polyurethane, polyvinyl pyrrolidone, polyvinyl acetate, polyvinyl alcohol, and polyvinyl alcohol-polyvinyl acetate copolymers, with polyurethane being the preferred film for the hair-treatment product of the present invention. While in the description which follows reference will be made only to polyurethane, it is to be understood that it is done so only to facilitate the discussion of the invention. Additionally, while the following description will only make reference to hair-waving compositions and products, it is also to be understood that the invention is not limited thereto since it could also be used for other hair-treatment applications, for example, in connection with hair-coloring, hair-straightening, and hair conditioning. In such alternative applications an effective amount of conventional ingredients used for such treatment of the hair would be similarly incorporated within the hydrophilic polymeric film.

The hydrophilic polyurethane film of the present invention is a flexible, dry film prior to its use and the hair-waving composition contained within the film is released from it upon its being contacted with wet hair.

While the hair-waving composition of the present invention can be any known and conventional composition employed in the waving of hair, it is preferable to employ a waving composition having a sulfur-containing compound as the active agent or ingredient. It is especially preferred to employ a sulfite or a bisulfite salt. It is most preferred to employ a mixture of a sulfite and a meta bisulfite salt. When a mixture of sulfite and bisulfite salts are employed the preferred ratio by weight is 1:1, although weight ratios of from about 1:10 to about 10:1 can be employed effectively, while the preferred pH of an aqueous solution of the hair-waving composition is in the range of from about 6 to about 7. The thickness of the polyurethane film can be from about 0.10 millimeters to about 0.50 millimeters with a range of from about 0.15 mm to about 0.34 being preferred, while a thickness of about 0.17 mm is especially preferred. The hair-waving composition may be present in the dry polyurethane film in the range of from about 20% to about 70%, by weight, with from about 40% to about 60%, by weight, being preferred.

A method of hair waving is also provided which comprises rolling the polyurethane film containing the hair-waving composition onto wet hair in the wave shape desired. Sufficient time is then allowed for the hair-waving composition to be released from the polyurethane film and to wave the hair.

DETAILED DESCRIPTION OF THE INVENTION

The hair-waving product of the present invention has two basic components; the first being the polyurethane film, and the second being the hair-waving composition. The polyurethane film can be any type of hydrophilic polyurethane film which is safe for human use and will not react with, or become decomposed by, the hair-waving composition. The properties of the polyurethane film can be varied according to the permanent wave desired. For example, if only a light permanent wave is desired, the polyurethane film may be manufactured having a relatively slow release rate of the hair-waving composition, or alternatively a relatively small amount of hair-waving composition. However, if a strong permanent wave is desired, a polyurethane film may be manufactured with a relatively high release rate of the hair-waving composition, or alternatively a relatively large amount of hair-waving composition.

The polyurethane film has the hair-waving composition entrapped therein. The polyurethane film is flexible and, prior to use, is maintained in a dry state. The dry form of the polyurethane film with the entrapped hair-waving composition avoids the problems of spillage or dripping of the hair-waving composition and, thus, decreases the potential for injury to the user. The hair-waving product of the present invention also provides a convenient package for the delivery of the hair-waving composition, eliminating guesswork as to the amount of hair-waving composition needed to achieve a given result. The use of sulfite and bisulfite actives essentially eliminates the malodor problem associated with perms containing thioglycolate actives. Because the hair-waving composition is mostly contained in the film during the waving process and is released directly at the point of application, the unpleasant odor associated with thioglycolate perming is significantly reduced. The preferred polyurethane film is manufactured in accordance with Example 1, which is discussed below.

The hair-waving composition may be any type which is known to wave the hair. Examples of hair-waving compositions are sulfite and bisulfite salts and mixtures thereof, such as sodium and amonium sulfite and meta bisulfite, the salts of thioglycollic acid, such as ammonium thiglycoate, calcium thioglycolate, the mercaptans, and other known sulfur-containing compounds used in hair waving, and mixtures thereof. The hair-waving composition is released from the film, after the film is contacted with wet hair.

Other materials may be included in the hair-waving composition, and thus entrapped therewith in the polyurethane film. For example, a pH adjuster can be added to the hair-waving composition to adjust its pH for safe and effective use. Ammonium hydroxide or amines can for instance be used to adjust the pH of a sulfite/bisulfite hair-waving composition to about 6 to 7. Additionally, other materials such as coloring materials or perfumes may be included in the hair-waving composition. Also, wetting agents and hair swelling agents may be added.

The hair-waving composition may be present in the polyurethane film in a concentration in the range of about 20% to about 70%, based upon the dry weight of the composition-containing film. The preferred concentration of hair-waving composition present in the polyurethane film is from about 40% to about 60%. However, the concentration of hair-waving composition in the polyurethane film is dependent upon the amount required to wave the particular individual's hair. Accordingly, polyurethane films having varying strengths, i.e., amounts of hair-waving composition and release rates, may be manufactured.

The hair-waving product may be manufactured by forming a solution or dispersion of a precursor of polyurethane, adding the hair-waving composition (and any other materials as desired) to the solution or dispersion, and forming a film of the desired thickness by, for example, casting from the solution or dispersion. Alternatively, the polyurethane film may be manufactured by any conventional method, e.g., extrusion, and the hair-waving composition can be impregnated into the polyurethane film, also by any conventional method. If extrusion is used, the polymer solid is mixed with the solid actives and other ingredients just prior to extrusion.

The thickness of the polyurethane film may vary depending upon the amount of hair-waving composition desired to be entrapped therein or depending on the flexibility of rigidity desired for the film. The thickness may be in the range of from about 0.10 mm to about 0.50 mm. Preferably, the thickness of the polyurethane film is in the range of from about 0.15 mm to about 0.34 mm. The polyurethane film may be shaped and cut into any desired configuration but is preferably configured into a generally rectangular strip, say, 3"×5", which facilitates its being rolled into the user's hair. The dimensions of the strip are dictated by the length of the user's hair.

The process of using the hair-waving product of the present invention comprises first separating the wet hair into small sections or swatches which are to be permed. Then a strip of polyurethane film, having the hair-waving composition entrapped therein, is folded lengthwise over a section of wet hair so that the hair is sandwiched between the folded segments of the strip which are the same length as the hair. The hair strip-sandwich is then configured, e.g., as by being rolled about a curler, into the desired wave shape. Optionally, the hair may be wetted again to facilitate the action of the perm.

The polyurethane film strip then releases the appropriate amount of hair-waving composition in a predetermined length of time, such as, for example, about 30 minutes, with or without the application of heat. After the hair-waving composition has been released, the hair may be rinsed in the usual manner to remove the hair-waving composition.

Thereafter, a neutralizing solution is applied to the hair, say, a solution of hydrogen peroxide. The neutralizer oxidizes the residual sulfite/bisulfite mixture on the hair that has not been removed by the rinse and also reforms the disulfide linkages that were broken in the waving process.

To illustrate how the hair-waving product may be manufactured, the following Example 1 sets forth a method whereby the product was produced.

EXAMPLE 1

Preparation of Polyurethane Film having Hair-Waving Composition Entrapped Therein The hydrophilic polyurethane polymers employed in the films of the present invention are formed by reacting polyoxyalkylene diols, as well as other diols, with a bifunctional diisocyanate, namely, methylene-bis-dicyclohexylisocyanate, which is manufactured by Mobay Chemical Corporation and sold under the trademarks Desmodur W or DW. During the reaction, urethane groups are formed, which give rise to long-chain polymers.

These long-chain hydrophilic polyurethane polymers, which are manufactured by Tyndale Plains-Hunter Ltd. of Princeton, N.J., and their methods of preparation are disclosed at greater length in U.S. Pat. Nos. 3,822,238, 3,975,350 and 4,789,720, all of which are incorporated herein by reference.

The specific Tyndale Plains-Hunter polymers employed in the Examples considered hereinafter are designated by them as D-3 and D-6, although other similar polymers and mixtures of polymers will provide acceptable results. The D-3 and D-6 polymers are formed in accordance with the above-described reaction, are hydroxy-terminated at both ends and differ only by the average molecular weight of the polyols used. The R-value of the D-3 and D-6 polymers is always less than 1, see Table 1 below, which is indicative of hydroxy-terminated polymers. The R-value is a measure of the ratio of NCO-groups to —OH groups.

TABLE 1

| Properties of D-3 and D-6 Polymers | | |
|---|---|---|
| | D-3 | D-6 |
| Wt. ratio of polyols:DW | 65:35 | 85:15 |

TABLE 1-continued

| Properties of D-3 and D-6 Polymers | | |
|---|---|---|
| | D-3 | D-6 |
| Av. MW of polyols | 500 | 1,855 |
| R-value | 0.98 | 0.94 |
| Water Content (%) | 68.0 | 82.0 |

Films of the D-3 and D-6 polymers having the hair-waving composition entrapped therein are formed by solution casting in accordance with the following procedure. The percentages, W/W, of the various ingredients are set forth below in Tables 2 and 3.

Initially, sodium sulfite and sodium meta bisulfite are crushed separately until they are of a size sufficient to pass through a 100 mesh screen. Thereafter, the solutions of the D-3 and D-6 polymers are mixed together. To the mixed polymers there is then slowly added, while maintaining continuous mixing:

water, until dissolved;
glycerin, until dissolved;
sodium sulfite, until dispersed;
sodium metal bisulfite, until dispersed; and
if swelling agents and/or surfactants are to be added, as is added to A in Example 2, infra, they are added at this point.

Once uniform dispersion has been achieved via mixing, 20–25 g of the mixture is quickly poured into a 7"×7" pan having a teflon-coated bottom to facilitate release. The mixture is allowed to dry overnight in a ventilated hood. After drying for 24 hours, the now dry polyurethane film, having the hair-waving composition dispersed therein, is peeled from the pan and cut into 3"×5" strips, or other appropriate sizes to accomodate hair length.

To illustrate how the hair-waving product of the present invention is used, the following Example 2 sets forth a method whereby hair is waved in accordance with the present invention.

EXAMPLE 2

A 5-inch, hair tress, weighing one gram, is shampooed and rinsed. A "3×5" polyurethane strip, prepared in accordance with Example 1, is folded over the wet tress and wound with a perm rod. The wound curl is wet with water, placed in a 30° C. oven and allowed to process for 30 or 60 minutes. After processing, the curl is rinsed for 5 minutes with running water, blotted dry and neutralized with a standard neutralizing solution for 10 minutes. Thereafter, the rod and strip are removed and the hair is rinsed briefly and allowed to dry at low heat under a dryer.

The degree of wave was compared with tresses treated with a standard marketed body wave product. The processing time for the marketed product is 60 minutes. Results were rated on the following scale:

0=no curl, 0.5=very poor curl, 1.0=poor curl, 1.5=poor to fair curl, 2.0=fair curl, 2.5=fair to good curl, 3.0=good curl, 3.5=good to excellent curl, 4.0=excellent curl (equal to marketed product), 4.5=better than marketed product.

Five tresses were used per experiment unless otherwise indicated.

TABLE 2

| | A | | B | |
|---|---|---|---|---|
| | Solution Concentrate % W/W | Dry Film % W/W | Solution Concentrate % W/W | Dry Film % W/W |
| D-3 Polymer (in 95% ETOH + 5% H₂O) | 17.74 | 11.30 | 16.92 | 9.17 |
| D-6 Polymer (in 95% ETOH + 5% H₂O) | 70.96 | 45.20 | 67.70 | 36.66 |
| Urea | 0.62 | 4.00 | | |
| Water | 4.47 | — | 5.40 | — |
| Glycerin | 1.77 | 11.30 | 1.80 | 9.75 |
| Sodium Sulfite | 2.22 | 14.10 | 4.09 | 22.21 |
| Sodium Meta Bisulfite | 2.22 | 14.10 | 4.09 | 22.21 |
| | 100.00 | 100.00 | 100.00 | 100.00 |
| *25.0 g of the above mixture was plated | | | | |
| Results: | | | | |
| 60 minutes: | 2.3 | | 3.7 | |
| 30 minutes: | — | | 3.3 | |

TABLE 3

| | A | |
|---|---|---|
| | Solution Concentrate % W/W | Dry Film % W/W |
| D-3 Polymer (in 95% ETOH + 5% H₂O) | 45.13 | 19.78 |
| D-6 Polymer (in 95% ETOH + 5% H₂O) | 36.93 | 16.19 |
| Water | 3.44 | — |
| Glycerin | 2.20 | 9.65 |
| Sodium Sulfite | 6.15 | 27.19 |
| Sodium Meta Bisulfite | 6.15 | 27.19 |
| | 100.00 | 100.00 |
| *20.0 g of the above mixture was plated | | |
| Results: | 30 minutes | 2.1 |

Although the present invention has been described in connection with preferred embodiments, many other variations and modifications will now become apparent to those skilled in the art without departing from the scope of the invention. The described variations were set forth for illustration purposes only and were not intended to be limiting. Additionally, throughout this specification and claims all percentages expressed are by weight, unless otherwise specified.

What is claimed is:

1. A hair-waving product to permanent wave the hair comprising a flexible, dry hydrophilic polyurethane film strip having a thickness in the range of about 0.10 to about 0.50 millimeters, said strip containing from about 20% to about 70% of a hair-waving composition comprising a salt of a sulfite, a bisulfite, or mixtures thereof, the hair-waving composition being releasable from the polyurethane film strip upon contact of the polyurethane film with wet hair to permanent wave the hair, said film strip remaining intact during the permanent waving.

2. A hair-waving product as claimed in claim 1, wherein the hair-waving composition comprises a 1:1, weight-by-weight, mixture of sodium sulfite and sodium meta bisulfite.

3. A hair-waving product as claimed in claim 2 wherein an aqueous solution of the hair-waving composition has a pH of from about 6 to about 7.

4. A hair-waving product as claimed in claim 1, wherein the hair-waving composition is present in the dry polyurethane film in the range of from about 40% to about 60%, by weight.

5. The hair-waving product as claimed in claim 1 wherein the polyurethane strip comprises from about 36% to about 56%, by weight, of the urethane polymer.

6. A method of permanent waving hair comprising rolling a flexible dry hydrophilic polyurethane film strip having a thickness in the range of about 0.10 to about 0.50 millimeters, said strip containing from about 20% to about 70% of a releasable hair-waving composition comprising a salt of a sulfite, a bisulfite, or mixtures thereof into wet hair, and allowing sufficient hair-waving time to release the hair-waving composition from the polymeric film strip to the wet hair to permanent wave the hair, said film strip remaining intact during the permanent waving.

7. The method of claim 6, wherein the hair-waving composition comprises a 1:1, weight-by-weight, mixture of sodium sulfite and sodium meta bisulfite.

8. The method of claim 7, wherein the hair-waving composition has a pH of from about 6 to about 7.

9. The method of claim 6, wherein the hair-waving composition is present in the dry polyurethane film in the range of from about 40% to about 60%, by weight.

10. The method of claim 6 wherein the polyurethane strip comprises from about 36% to about 56%, by weight, of the urethane polymer.

* * * * *